(12) United States Patent
Flocken et al.

(10) Patent No.: US 10,233,102 B2
(45) Date of Patent: Mar. 19, 2019

(54) DEVICE AND METHOD FOR CONTROLLING DEPOSIT FORMATION

(71) Applicant: Solenis Technlogies, L.P., Schaffhausen (CH)

(72) Inventors: Christian Flocken, Krefeld (DE); Frank Seida, Werne (DE)

(73) Assignee: SOLENIS TECHNOLOGIES, L.P., Schaffhausen (CH)

(*) Notice: Subject to any disclaimer, the term of this patent is extended or adjusted under 35 U.S.C. 154(b) by 290 days.

(21) Appl. No.: 15/105,352

(22) PCT Filed: Dec. 29, 2014

(86) PCT No.: PCT/EP2014/079378
§ 371 (c)(1),
(2) Date: Jun. 16, 2016

(87) PCT Pub. No.: WO2015/101603
PCT Pub. Date: Jul. 9, 2015

(65) Prior Publication Data
US 2016/0311714 A1    Oct. 27, 2016

(30) Foreign Application Priority Data

Jan. 3, 2014  (EP) .................................... 14150149

(51) Int. Cl.
*C02F 1/00* (2006.01)
*C02F 5/02* (2006.01)
(Continued)

(52) U.S. Cl.
CPC ................ *C02F 5/02* (2013.01); *C02F 1/008* (2013.01); *G01N 29/024* (2013.01);
(Continued)

(58) Field of Classification Search
CPC .... C02F 1/008; C02F 1/00; C02F 1/66; C02F 1/68; C02F 1/685; C02F 1/50
(Continued)

(56) References Cited

U.S. PATENT DOCUMENTS 5,057,229 A * 10/1991 Schulenburg .......... C02F 1/008
  210/139
5,114,571 A   5/1992 Pier et al.
(Continued)

FOREIGN PATENT DOCUMENTS

DE        2009012876      4/2010
DE    202009012876 U1     4/2010
(Continued)

OTHER PUBLICATIONS

International Search Report, PCT/EP2014/079378, dated Mar. 4, 2015, pp. 2.
(Continued)

*Primary Examiner* — Ellen M McAvoy
(74) *Attorney, Agent, or Firm* — Lorenz & Kopf, LLP (57) ABSTRACT

The invention suggests a method for controlling the deposit formation in a main system of a liquid bearing system, wherein a liquid is transported inside the liquid bearing system, wherein the liquid bearing system comprises a main system and a subsystem, wherein the subsystem is configured such that a tendency of deposit formation is promoted more inside the subsystem than inside the main system.

13 Claims, 4 Drawing Sheets

(51) Int. Cl.
*G01N 29/024* (2006.01)
*C02F 103/02* (2006.01)
*G01B 17/02* (2006.01)

(52) U.S. Cl.
CPC .. *C02F 2103/023* (2013.01); *C02F 2209/001* (2013.01); *C02F 2209/02* (2013.01); *C02F 2209/40* (2013.01); *C02F 2209/44* (2013.01); *C02F 2303/22* (2013.01); *G01B 17/025* (2013.01); *G01N 2291/022* (2013.01); *G01N 2291/0258* (2013.01); *G01N 2291/02854* (2013.01); *G01N 2291/044* (2013.01)

(58) Field of Classification Search
USPC ................................................ 210/205, 206
See application file for complete search history.

(56) References Cited

U.S. PATENT DOCUMENTS

| | | | | |
|---|---|---|---|---|
| 5,422,014 | A * | 6/1995 | Allen | C02F 1/008 210/139 |
| 9,409,110 | B2 * | 8/2016 | Urmenyi | B01D 37/041 |
| 2005/0109703 | A1 | 5/2005 | Newenhizen et al. | |
| 2008/0053204 | A1 | 3/2008 | Neville et al. | |
| 2009/0035180 | A1 * | 2/2009 | Wan | C02F 1/008 422/62 |
| 2009/0277841 | A1 * | 11/2009 | Johnson | F28F 19/00 210/668 |
| 2010/0176060 | A1 | 7/2010 | Duarte et al. | |
| 2010/0243570 | A1 | 9/2010 | Mayer et al. | |
| 2013/0026105 | A1 | 1/2013 | Duarte et al. | |
| 2015/0151982 | A1 * | 6/2015 | Ferrari | C02F 1/008 210/739 |

FOREIGN PATENT DOCUMENTS

| | | |
|---|---|---|
| WO | 2009141135 | 11/2009 |
| WO | 2013092819 | 6/2013 |
| WO | 2013092820 | 6/2013 |

OTHER PUBLICATIONS

National Institute of Industrial Property Ministry of Economy, Official Action in Chilean Patent Application No. 201601681 dated Apr. 17, 2018.
European Patent Office International Preliminary Examining Authority, International Preliminary Report on Patentability in International Application No. PCT/EP2014/079378 dated Apr. 1, 2016.
Korean Intellectual Property Office (KIPO) Notice of Preliminary Rejection, Application No. 10-2016-7020895, dated Oct. 19, 2017.

* cited by examiner

DEVICE AND METHOD FOR CONTROLLING DEPOSIT FORMATION

FIELD OF THE INVENTION

The invention relates to the deposit control in water bearing systems, particularly in open recirculating cooling water systems.

BACKGROUND

Open recirculating cooling water systems are widely used processes for rejection of waste heat from a variety of industrial processes. Such systems are open as water e.g. evaporates at the cooling tower. In addition, controlled removal of recirculating water is necessary to limit the accumulation of dissolved species that cause corrosion, scaling and fouling. The effluent water is removed with the so-called "blowdown stream".

Various additives are on the market that can be added to the recirculating water in order to specifically avoid corrosion, scaling or fouling. These additives are normally fed at a feeding rate needed to maintain a relatively constant concentration in the recirculating water. The feeding rate is typically controlled to replace the amount of the additives that are consumed within the recirculating system and that are removed with the blowdown stream.

However, this type of deposit control is static and cannot properly react when the composition of the recirculating water changes unexpectedly. Such unexpected changes can have various causes. For example, the temperature and thus also the composition of the fresh water (makeup water) that is added to the system varies over the year.

Various attempts have been made to monitor the properties of the recirculating water in order to better understand the processes taking place and to properly react in case of unexpected events. All these attempts rely on the monitoring of one or more key operation indicators such as pH value of the recirculating water, electrical conductivity of the recirculating water, concentration of anti-deposit additives in the recirculating water.

Based upon the measured values of these key operation indicators, conclusions are drawn in respect of the current tendency of the recirculating water to form deposits. If necessary, counter measures are initiated that are believed to be appropriate, such as increasing the dosage of a particular anti-deposit additive. Attempts have also been made to simultaneously monitor a plurality of key operation indicators in order to base the initiated counter measure on a broader basis of data.

However, key operation indicators such as pH value, electrical conductivity, and the like are not directly linked to deposit formation. Even if electrical conductivity and pH value are stable over time, undesired scaling may occur. Ongoing processes may compensate one another. For example, when the pH value is decreased for some reason, this may lead to an increase of the concentration of e.g. basic $CaCO_3$ in the recirculating water thus increasing the pH value again. Furthermore, a sudden change of the pH value, for example, can have various reasons. The pump that supplies acid or base to the recirculating water may be broken, the pH meter may be broken, the storage tank containing acid, base or buffer may be empty, and the like. Therefore, a key operation indicator may change for various reasons that all have the same consequence of undesired deposit formation.

US 2009/0277841 discloses a process for operation of evaporative recirculating cooling systems. In addition to reducing the scaling and corrosive tendencies of the water, the method is said to eliminate or reduce discharge from the system without creating any localized corrosive or scaling conditions as a result of the treatment process. The described measurement and control system generally comprises an array of measurements, a means of implementing control logic, and an array of control actions including activating an ion exchange device to treat makeup water. Preferably, the measurements include one or more of pH, conductivity, hardness, alkalinity, corrosiveness, scaling tendency, treatment additive dosage level, and treatment additive residual of the makeup, treated makeup, and recirculating water.

US 2010/0176060 and US 2013/0026105 disclose the control of scaling in a cooling water system with $CO_2$ based upon measurements of the cooling water's pH, alkalinity and $Ca^{2+}$ concentration.

A further problem is that the formation of certain deposits is irreversible. This is particularly the case for scaling. While sophisticated anti-scaling additives are available on the market that are capable of effectively avoiding the deposition of the scaling on surfaces at appropriate dosages, they are usually not capable of removing the scaling once it has been deposited. In consequence, the dosage of anti-scaling additives in the recirculating water is typically kept higher than really necessary in order to avoid scaling formation, just to ensure that no scaling is irreversibly formed.

SUMMARY OF THE INVENTION

There is a demand for methods to control deposit formation, in particular scaling, in water bearing systems and to initiate appropriate countermeasures that have advantages compared to the methods of the prior art.

The object of the present invention is solved by a method for controlling deposit formation in a liquid bearing system comprising a main system and a subsystem, wherein a liquid is transported inside the main system and/or the subsystem, the method comprising the step of altering a property of the liquid inside the subsystem such that it differs from the property of the liquid inside the main system in a manner that deposit formation inside the subsystem is more promoted than inside the main system.

It is herewith advantageously possible to use the subsystem as a watchdog or as an early warning system, because it has been surprisingly found that artificial process conditions can be established that promote deposit formation, i.e. that are harsher process conditions with respect to deposit formation. Thus, the liquid that is processed under such harsher process conditions tends to form deposits, in particular scaling, inside the subsystem ahead of the recirculating liquid that is processed under the current operational conditions of the liquid bearing system inside the main system. Such a method may ensure that a proper countermeasure is initiated before deposit formation inside the main system of the liquid bearing system even starts. In particular, the main system and the subsystem are configured such that the liquid has access to both the main system and the subsystem. As a result the concentration of a treatment chemical inside the subsystem is the same as the concentration of the treatment chemical inside the main system advantageously. The treatment chemical may be configured such that the treatment chemical comprises antideposit components. Moreover it is provided that the liquid is recirculated inside the liquid bearing system. Preferably the liquid comprises water and the liquid bearing system comprises a cooling tower or a tank. Deposits are for example scale, fouling and/or corrosion products such as iron oxides. In particular the treatment chemical comprises antisling products, antifouling products and/or anticorrosion products. Furthermore it is provided that the countermeasure is adapted to the kind of deposit. As a consequence the composition of the treatment chemical may be adapted to the kind of deposit. For example the treatment chemical comprises an antifouling component that reduces the specific fouling detected inside the subsystem. It is also thinkable that the chemical treatment is fed to the liquid bearing system at a feeding rate, wherein the feeding rate depends on the type of the deposit. In particular it is thinkable that the treatment chemical is fed to the liquid bearing system in a continuous or pulsed form. Moreover it is provided that treatment chemicals are fed to the liquid bearing system all the time, wherein the composition of the treatment chemical is changed as soon deposit formation is detected inside the subsystem. Further it has been surprisingly found that the artificial process conditions can be adjusted over a broad range so that different degrees of harshness are possible. In consequence, a buffer between the harsher conditions in the bypass and the current conditions in the operational water bearing system can be freely adjusted to allow for a comparatively early or for a comparatively late initiation of counter measure, respectively. It is also conceivable that the deposit formation is derived from detecting a key operation indicator such as pH value, electrical conductivity and the like. Furthermore it is provided that the pipes of the main system and the subsystem are made from the same material.

In another embodiment of the present invention it is provided that the subsystem comprises a detection device for detecting the deposit formation. Consequently it is advantageously possible to detect a key performance indicator directly. For the purpose of the specification, a key performance indicator according to the invention is a property that is directly linked to the presence or absence of a deposit, particularly corrosion, scaling, and/or fouling. It has been surprisingly found that deposit control can be substantially improved when it is not based on monitoring of key operation indicators such as the pH-value, but on monitoring of key performance indicators instead, namely deposit formation, as corrosion, scaling and fouling for instance. It is principally also possible to get information about a key performance indicator by measuring the temperature, in particular its heat transfer coefficient, of a material that is exposed to the water bearing system such that a deposit may be formed on its surface. For example, it is known that measuring the temperature or more precisely the heat transfer coefficient at various locations of a heat exchanger may provide information about deposit formation due to changes of heat capacity and thermal conductivity. Key performance indicators, i.e. deposits, may be detected by various means, e.g. optically, electrically, mechanically or with X-rays. It is also thinkable that the subsystem is configured such that the subsystem may be uncoupled from the main system. Subsequently the subsystem is examined for deposit formation and/or type of the deposit without stopping the operation of the main system advantageously.

In another embodiment it is provided that the subsystem is a bypass. It has been surprisingly found that the monitoring of key performance indicators can advantageously be performed in a bypass wherein artificial process conditions that promote deposit formation are set inside the bypass. Once a significant change of key performance indicators is detected under the artificial conditions within the bypass, e.g. the beginning of scaling, appropriate countermeasures may be initiated, e.g. by increasing the dosage of anti-scaling additive. As the environment in the bypass is more favorable for deposit formation than in the main system, scaling has not yet begun in the main system and can thus be effectively prevented. This has particularly advantageous with respect to scaling which can usually not be removed by means of anti-scaling additives once it has been deposited on a surface. Preferably, the condition of the liquid, in particular of recirculating water, in the bypass differs from the condition of the liquid in the main system. Preferably, the temperature and/or the flow velocity of the recirculating water in the bypass is/are higher than that of the recirculating water in the main system.

In another embodiment of the present invention it is provided at least one property of the liquid inside the subsystem is manipulated by a manipulation device. Preferably the liquid inside the subsystem and the liquid in the main system have only one non-equivalent property. As a consequence the subsystem represents the main system as closely as possible advantageously. Furthermore, it has been surprisingly found that artificial process conditions can be established without substantially altering the thermal conditions of the system. In particular, it has been surprisingly found that the temperature of the recirculating water in the bypass does not need to be changed compared to the temperature of the recirculating water in the operational water bearing system.

In another embodiment of the present invention it is provided that liquid inside the subsystem is configured such that a Reynolds number of the liquid inside the subsystem is greater than 8,000 and preferably between 10,000 and 20,000. It has been surprisingly found that the deposit formation will be accelerated, if the Reynolds number is greater inside the subsystem than inside the main system and the Reynolds number inside the subsystem is greater than 8,000 and preferably between 10,000 and 20,000. Preferably, the stream inside the bypass is not laminar but turbulent, whereas the stream in main system is not turbulent but laminar. Typically the Reynolds number depends on the density, the viscosity, the flow velocity and the dimensions of the liquid.

In another embodiment of the present invention it is provided that a first flow velocity of the liquid inside the subsystem is configured such that the first flow velocity inside the subsystem is greater than a second flow velocity inside in the main system. Preferably the volume flow of the liquid in the bypass is higher than that of the liquid in the main system. Preferably, the volume flow or the first velocity in the bypass is higher by at least 0.01 m/sec, more preferably by at least 0.05 m/sec, still more preferably by at least 0.1 m/sec, yet more preferably by at least 0.15 m/sec., most preferably by at least 0.2 m/sec, and in particular by at least 0.25 m/sec than the flow velocity of the liquid in the main system. Preferably, the temperature of the recirculating water in the bypass does not significantly differ from the temperature of the recirculating water in the operational water bearing system. Preferably, the temperature difference is not more than 1° C., more preferably not more than 0.5° C., most preferably not more than 0.2° C.

In another embodiment of the present invention it is provided that the first flow velocity inside the subsystem is mainly realized by a pumping device. In particular the flow velocity may easily be adjusted by a suitable pump inside the bypass. It has been surprisingly found that the kinetic energy entrained by the pump in order to increase the first flow velocity of the liquid in the bypass is much lower than the energy that would otherwise be entrained by increasing the water temperature in the bypass. In a preferred embodiment it is provided to manipulate the flow velocity by hydrostatic or hydrodynamic means. In particular a hydrostatic, hydrodynamic or atmospheric pressure of the main system is only used for acceleration. Thus, when guiding the recirculating water through the bypass at an elevated flow velocity but constant temperature, the thermodynamic conditions inside the bypass are very similar to the thermodynamic conditions in the operational water bearing system. Thus the current situation in the main system is very closely reflected by the current situation in the bypass at favored conditions with respect to deposit formation.

In a preferred embodiment of the present invention it is provided that the deposit formation is detected by means of ultrasound, wherein an ultrasonic signal is emitted and a reflected ultrasonic signal is detected. Preferably the measurement provides information about the thickness and/or composition of the deposit. Suitable methods and devices to measure key performance indicators by means of ultrasound are known from the prior art. These methods and devices preferably also monitor the temperature so that additional conclusions can be drawn from the temperature values.

In particular it is provided that the deposit is detected by a device, for detecting deposits in a reflection area inside a liquid-bearing system comprising an ultrasonic transducer for emitting an ultrasonic emission signal towards the reflection area and a first detection means for detecting an ultrasonic reflection signal obtained by reflection of the ultrasonic emission signal in the reflection area, wherein a second detection means is disposed in the reflection area, the second detection means being configured to detect a specific kind of deposit. It is also possible to detect the deposit by a method for detecting fouling and/or scaling deposits in a reflection area inside the liquid-bearing system, comprising a first step of emitting the ultrasonic emission signal towards the reflection area by an ultrasonic transducer, a second step of detecting an ultrasonic reflection signal obtained by reflection of the ultrasonic emission signal in the reflection area by first detection means and a third step of detecting a specific kind of deposit by a second detection means disposed in the reflection area. It is herewith advantageously possible to identify the type or kind or composition of the deposit and subsequently adapt the treatment chemical to the kind of deposit.

In another preferred embodiment it is provided that the deposit formation inside the subsystem is detected by one of the methods disclosed in WO 2009/141 135. Preferably the deposit formation is detected by a method for a high precision measurement of a characteristic of a fouling and/or scaling deposit inside a fluid pipe or of a characteristic of a portion of the wall inside a fluid pipe, wherein an ultrasonic transducer is used, wherein a reflection area is provided in a portion of the wall or attached to a portion of the wall of the fluid pipe at a location substantially opposite of the ultrasonic transducer, wherein the method comprises the steps of:
a) emitting an ultrasonic emission signal by means of the ultrasonic transducer and
b) measuring the distance between the ultrasonic transducer on the one hand and a fluid/deposit interface or a fluid/wall interface on the other hand in an absolute distance measurement by means of evaluating the time-domain reflective signal of the fluid/deposit or fluid/wall interface, wherein the fluid/deposit or fluid/wall interface is either the interface of the fluid with the deposit on the reflection area or the interface of the fluid with the wall in the reflection area, wherein the time-domain resolution power is 1 ns or less than 1 ns. Preferably the deposit is detected by one of the devices disclosed in WO 2009/141 135. In particular it is disclosed a device for a high precision measurement of a characteristic of a fouling and/or scaling deposit inside a fluid pipe or of a characteristic of a portion of the wall inside a fluid pipe, wherein the device comprises an ultrasonic transducer, wherein the device further comprises a reflection area in a portion of the wall or attached to a portion of the wall of the fluid pipe at a location substantially opposite of the ultrasonic transducer, wherein the distance between the ultrasonic transducer on the one hand and a fluid/deposit interface or a fluid/wall interface on the other hand is measured in an absolute distance measurement by means of evaluating the time-domain reflective signal of the fluid/deposit or fluid/wall interface, wherein the fluid/deposit or fluid/wall interface is either the interface of the fluid with the deposit on the reflection area or the interface of the fluid with the wall in the reflection area, wherein the time-domain resolution power of the device is 1 ns or less than 1 ns.

In another preferred embodiment of the present invention it is provided that the deposit inside the subsystem is detected by one of the methods disclosed in WO 2013/092 819. In particular the method for detecting deposit formation comprises a method for detecting and analyzing deposits on the reflecting area, in particular inside the liquid-bearing system, comprising the steps of:
  emitting the ultrasonic emission signal towards the reflecting area by an ultrasonic transducer in a further first step;
  detecting an ultrasonic reflection signal obtained by reflection of the ultrasonic emission signal in the area of the reflecting area by detection means in a further second step;
  determining a distribution of the run time of the detected ultrasonic reflection signal in response to a specified variable in a further third step;
  analyzing the distribution in a fourth step in order to determine if deposits are deposited at least partially onto the reflecting area. WO 2013/092819 also discloses devices for detecting and analyzing deposits in a reflecting are. These devices may be attached to the subsystem in order to detect deposit formation. Preferably the device comprises an ultrasonic transducer for emitting an ultrasonic emission signal towards the reflecting area, a detection means for detecting an ultrasonic reflection signal obtained by reflection of the ultrasonic emission signal in the area of the reflecting area and an analyzing unit for determining a distribution of the run 5 time of the detected ultrasonic reflection signal in response to a specified variable and for analyzing the distribution in order to determine if deposits are deposited at least partially onto the reflecting area.

In another particularly preferred embodiment of the present invention the deposit formation is detected by one of devices disclosed in WO 2013/092820. In particular the device for detecting the deposit comprise a device for detecting deposits in a reflecting area inside a liquid-bearing system comprising an ultrasonic transducer for emitting an ultrasonic 5 emission signal towards the reflecting area and a detection means for detecting an ultrasonic reflection signal obtained by reflection of the ultrasonic emission signal in the area of the reflecting area, wherein the device further comprises a heater for increasing the temperature of the reflecting area. WO 2013/092820 also discloses a method for detecting fouling and/or scaling deposits in a reflecting area, in particular inside a liquid-bearing system, comprising a step of emitting an ultrasonic emission signal towards the reflecting area by an ultrasonic transducer and a step of detecting an ultrasonic reflection signal obtained by reflection of the ultrasonic emission signal in the area of the reflecting area by detection means, wherein the temperature of the reflecting area is increased by the heater. Preferably the deposit is measured by one of the methods disclosed in WO 2013/092820.

In a preferred embodiment of the present invention it is provided that the concentration of the treatment chemicals inside the liquid bearing system is continuously or stepwise decreased, in particular following a mathematical function. In particular the decrease continues till deposit formation is detected inside the subsystem. Furthermore it is provided that the concentration of the treatment chemicals inside the liquid bearing system is manipulated, in particular decreased, every time interval, wherein the time interval corresponds to a dwell time. Preferably the dwell time is set by basic parameters describing the liquid bearing system such as the total volume of the liquid inside the liquid bearing system and the loss of liquid during the running of the liquid bearing system. In particular it is provided that the concentration of the treatment chemical inside the liquid bearing system is regulated by manipulating the amount of treatment chemicals and/or liquid being fed to the liquid bearing system in order to compensate the loss of treatment chemicals and/or liquid during running the liquid bearing system. Furthermore it is provided that the concentration of the treatment chemical, in particular an antiscaling product, inside the liquid bearing system is increased as soon a deposit formation inside the subsystem is detected. Preferably the amount of treatment chemicals fed to the liquid bearing system is a multiple, in particular the double, of the amount of treatment chemicals that were fed to the liquid bearing system in a previous time interval. Furthermore it is provided that the concentration of the treatment chemical inside the liquid bearing system is decreased again after the concentration of the treatment chemical was decreased in the previous time interval.

In another embodiment of the present invention it is provided that the temperature inside the subsystem is monitored. In particular the temperature at the wall of the pipe guiding the liquid through the bypass is monitored. The temperature may be used for controlling the temperature inside the subsystem positively. It is also thinkable that the detected temperature may indicate the deposit formation.

In another embodiment of the present invention it is provided that the subsystem comprises a heater. Such a heater may heat the liquid in the subsystem. As a result it is advantageously possible to simulate the thermodynamic condition of a part of the main system being far away from the subsystem, wherein the liquid inside the part of the main system has a higher temperature than the liquid inside an unheated subsystem. Such parts of the main system are for example parts of the main system that are responsible for a heat exchange. The temperature of the part of the main system being far away from the subsystem favors deposit formation inside the part of the main system compared to those parts of the main system having a lower temperature. Equalizing the thermodynamic conditions of the liquid inside the subsystem and inside the part of the main system being far away from the substrate may guarantee that the subsystem even operates as an early warning system for parts of the main system that are usually favored for deposit formation.

In another embodiment of the present invention it is provided that the liquid bearing system comprises a device for monitoring the temperature at a wall of a pipe, wherein the liquid is guided by the pipe, wherein the device for monitoring the temperature at the wall of the pipe comprises a first mean for measuring a first temperature at a first spot and a second mean for measuring a second temperature at a second spot, wherein the first spot is spaced from the wall of the pipe by a first distance and the second spot is spaced from the wall of the pipe by a second distance, wherein the second distance is greater than the first distance and wherein the temperature is approximated based on the first temperature and the second temperature. Preferably the device for monitoring the temperature at the wall of the pipe is arranged to the subsystem. It is herewith advantageously possible to approximate the temperature of the liquid inside the liquid bearing system or at the wall of the pipe without using a device that may influence the stream inside the liquid bearing system, in particular inside the subsystem. Moreover it is advantageously it is possible to adapt the device for monitoring the temperature to the pipe without a recess inside the pipe, wherein the recess is intended or receiving the device for monitoring the temperature. As a result it is possible to realize a preferably robust subsystem. It is also thinkable that the first and the second mean for measuring the temperature are included in a common body. Moreover it is provided that the heater and the device for monitoring the temperature form an unit.

In another embodiment it is provided that the liquid bearing system is a cooling water system having an outflow and an inflow, wherein water is transported inside the main system and/or the subsystem, wherein the subsystem is a bypass, the method comprising the step of altering a property of the water inside the bypass such that it differs from the property of the water inside the main system in a manner that scaling formation inside the subsystem is more promoted than inside the main system, wherein a first flow velocity of the liquid inside the subsystem is greater than a second flow velocity inside the main system, wherein the Reynolds number of the water inside the subsystem is between 10,000 and 20,000, wherein the scaling formation inside the subsystem is detected by means of ultrasound, wherein an ultrasonic signal is emitted and a reflected ultrasonic signal is detected. Furthermore it is thinkable that the temperature inside the subsystem is adapted by a heater.

In another embodiment it is provided that an additional treatment chemical is fed to the liquid bearing system as soon as a deposit inside the subsystem is detected.

Another subject of the present invention is a device for controlling deposit formation in a liquid bearing system comprising a main system and a subsystem, wherein a liquid is transportable inside the main system and/or the subsystem, wherein the device is configured for altering a property of the liquid inside the subsystem such that it differs from the property of the liquid inside the main system in a manner that deposit formation inside the subsystem is more promoted than inside the main system.

It is herewith advantageously possible to detect and/or identify deposit inside the subsystem and timely react by initiating countermeasures in order to avoid deposit formation inside the main system.

Another subject is an upgrade kit for a liquid bearing system, wherein the upgrade kit comprises a device as described above and a subsystem.

It is herewith advantageously possible to mount the subsystem to the liquid bearing system easily. As a result the mounted upgrade may identify timely deposit formation, in particular scaling, inside the subsystem and therefore proper countermeasures may be started in order to avoid deposit formation inside the liquid bearing system.

These and other characteristics, features and advantages of the present invention will become apparent from the following detailed description, taken in conjunction with the accompanying drawings, which illustrate, by way of example, the principles of the invention. The description is given for the sake of example only, without limiting the scope of the invention. The reference figures quoted below refer to the attached drawings.

DETAILED DESCRIPTION OF THE INVENTION

The present invention will be descripted with respect to particular embodiments and with the reference to certain drawings but the invention is not limited thereto but only by the claims. The drawings described are only schematic and are non-limiting. In the drawings, the size of some elements may be exaggerated and not drawn on scale for illustrative purposes.

Where an indefinite or definite article is used when referring to a singular noun, e. G. "a", "an", "the", this includes a plurals of the noun unless something else is specifically stated.

Furthermore, the terms first, second, third and the like in the description and in the claims are used to distinguishing between similar elements and not necessarily for describing a sequential or chronological order. It is to be understood that the terms so used are interchangeable under appropriate circumstances and that the embodiments of the invention described herein are capable of operation in other sequences than described of illustrated herein.

Figure 1:
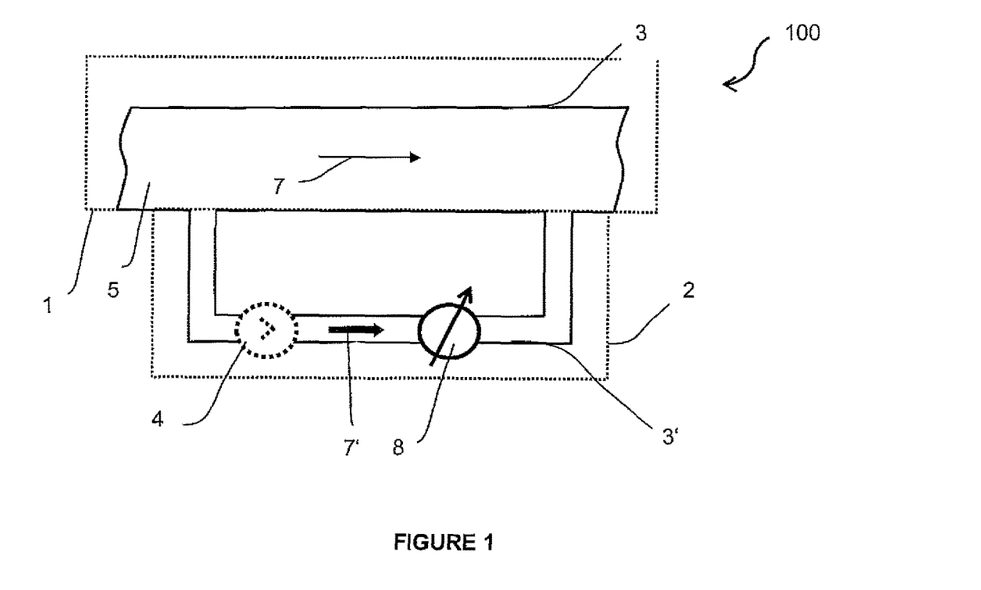
FIG. 1 shows a first exemplary embodiment of the method according to the present invention.

In FIG. 1 a first exemplary embodiment of a method for controlling deposit 60 formation in a liquid bearing 100 system according to the present invention is illustrated. It is provided that a liquid 5, in particular water, inside the liquid bearing system 100 is transported, in particular recirculated through the liquid bearing system 100. According to the present invention it is provided that the liquid bearing system 100 comprises a main system 1 and a subsystem 2. In particular the main system 1 comprises a pipe 3 for guiding the liquid 5. It is also thinkable that the main system 1 also comprises other components such as a tank, a cooling water tower, a cooling or process system. Moreover it is provided that the subsystem 2 is configured as a bypass, i. e. a stream of the liquid 5 is guided in a separated pipe 3' bypassing the remainder of the liquid 5 that remains inside the main system 1 of the liquid bearing system 100. As a consequence the liquid 5 inside the subsystem 2 is mainly equivalent to the liquid 5 inside the main system 1. For example the liquid 5 inside the subsystem 2 has the same concentration of treatment chemicals compared to the liquid 5 inside the main system 1. According to the present invention it is provided that the liquid bearing system 100 is configured such that the liquid 5 inside the subsystem 2 has a promoted tendency for forming deposit 60 compared with the liquid 5 inside the main system 1. As a result the deposit 60 is formed firstly in the subsystem 2. Preferably the subsystem 2 comprises a detection device 8 for detecting deposit 60 formation and consequently it is advantageously possible to detect deposit 60 inside the subsystem 2 before deposit 60 formation starts inside the main system 1 of the liquid bearing system 100. In other words: The subsystem 2 according to the present invention and the detection device for detecting deposit formation forms a watchdog or an early warning system for the main system 1 of the liquid bearing system 100. In particular it is provided that the detection of deposit 60 inside the subsystem 2 starts a countermeasure that prevents the deposit 60 formation inside the main system 1 advantageously. For instance an antiscaling product is fed to the liquid bearing system 100 immediately in order to avoid scaling from the beginning inside the liquid bearing system 100. It is also conceivable that there is an extra portion of treatment chemicals provided for being fed to the liquid bearing system 100 as soon as a growth of the deposit 60 is detected in the subsystem 2. Optionally the subsystem 2 comprises a pumping device 4. The pumping device 4 accelerates the liquid 5 inside the subsystem 2 of the liquid bearing system 100. Preferably a hydrostatic or hydrodynamic pressure from the main 100 is used for acceleration as well instead of the pumping device. Therefore the volume flow of the liquid 5 inside the subsystem 2 leaving the pumping device 4 has a first velocity, wherein in the first velocity is greater than a second velocity representing the volume flow of the liquid 5 in the main system 1. It has surprisingly found that tendency of deposit 60 formation can be increased by increasing the volume flow or the flow velocity respectively. As a result the subsystem 2 according to the first exemplary embodiment is configured such that the tendency of forming deposit 60 inside the subsystem 2 is greater in the subsystem 2 than inside the main system 1, wherein the thermal conditions are constant mainly.

Figure 2:
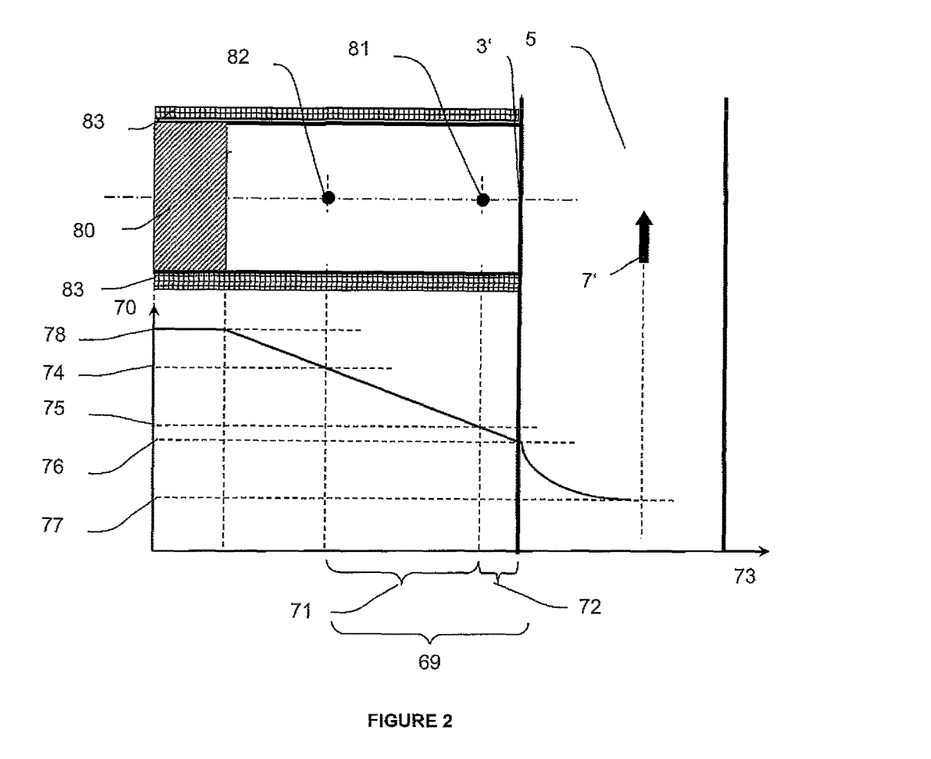
FIG. 2 shows a first exemplary embodiment of the method according to the present invention.

In FIG. 2 a second exemplary embodiment of a method according the present invention is illustrated schematically. The second exemplary embodiment supplements the first exemplary embodiment by a heater 80 and a device for monitoring the temperature at the wall of the pipe 3. In particular FIG. 2 shows a part of the subsystem 1 including the heater 80 and the device for monitoring the temperature at the wall of the pipe. Preferably the liquid 5 inside the subsystem 2 is equal as possible to the liquid 5 inside the main system 1 in order to provide comparable conditions for deposit formation inside the main system 1 and the subsystem 2. It has surprisingly found that the tendency of deposit 60 formation can be influenced by the temperature of the liquid 5. In particular a tendency of fouling formation is increased with increasing temperature. Due to the configuration of the subsystem 2 the temperature inside the subsystem 2 may not be equivalent to the temperature inside the main system 1. In particular it is provided that a device for monitoring the temperature mounted at the wall of the pipe 3,3' determinate the temperature at the wall of the pipe 3,3'. For this purpose a first mean 81 for measuring a first temperature 75 is located at a first spot being spaced by a first distance 69 from the wall of the pipe 3,3'. Additionally a second mean 82 for measuring a second temperature 74 is localized at a second spot being spaced by a second distance from the wall of the pipe 3,3'. Preferably the second distance 72 is greater than the first distance 75 and/or the first mean 81 for measuring the first temperature 75 and the second mean 82 for measuring the second temperature 74 are included in a common body that has a homogenous thermal conductivity. Moreover the first spot and the second spot are localized between the wall of the pipe 3,3' and the heater 80. Provided that a temperature at the heater 78 differs from the temperature 76 at the wall of the pipe the temperature gradually changes from the heater 80 to the wall of the pipe 3,3' as it is illustrated in the plot, placed on the left side of FIG. 2. The plot shows the temperature 70 in dependency of the distance 73. Due to the linear relationship between distance 73 and temperature 70 it is advantageously possible to approximate the temperature 76 at the wall of the pipe based on the first temperature 75 and the second temperature 74. Preferably the approximation of the temperature 71 at the wall takes also into account the first and the second distance 69 and 72. In particular the temperature at the wall of the pipe is extrapolated from the first temperature 75 in the first spot and the second temperature 74 at the second spot. Moreover it is conceivable that the temperature profile inside the pipe 3,3', in particular along a direction perpendicular to the wall of the pipe, is known and therefore the temperature 77 at a center line 51 of the pipe 3,3' may be also approximated. Furthermore it is provided that a third distance 71 between the first spot and the second spot is greater than the thickness of the wall of the pipe 3,3.

Figure 3:
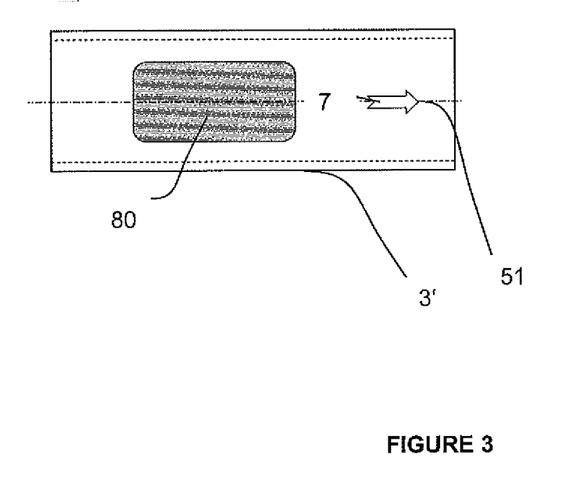
FIG. 3 shows a first exemplary embodiment of the method according to the present invention.

In FIG. 3 a third embodiment of the method for controlling deposit 60 formation according to the present invention is illustrated. According to the third embodiment the subsystem 2 is at least partially shaped as a cuboid. Preferably the heater 80 is located symmetrical to the center line 51 of the subsystem, i.e. a symmetry axis of the heater 80 is located at the center line of the subsystem 2.

Figure 4:
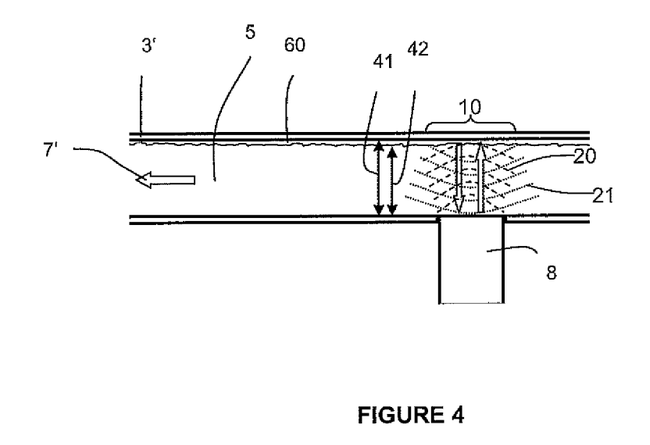
FIG. 4 shows an exemplary device for detection deposit formation arranged to a pipe.

In FIG. 4 is an exemplary device for detection deposit 60 formation is illustrated, wherein the device for deposit detection 8 is mounted to the pipe. Preferably the pipe 3 has a cylindrical body and the liquid 5 is transported along a transport direction 7. Typically deposit 60 formation occurs on an inner surface of the pipes 3 of the subsystem 2. Preferably the device for deposit detection 8 is attached to the pipe 3. In particular the device for detecting deposit formation 8, in particular scaling, comprises a mean for emitting an ultrasonic signal and a mean for detecting a reflected ultrasonic signal. Preferably an ultrasonic transducer emits am emitted ultrasonic signal 20, subsequently the emitted ultrasonic signal 20 is transformed to a reflected ultrasonic signal 21 by reflection from a reflection area 10 and finally the ultrasonic signal is detected by the detection means. Preferably the reflection area 10 is located opposite to the device for detecting deposit 8, in particular scale. Based on the travel time of the ultrasonic signal it is possible to measure an effective diameter of the pipe 42, wherein the effective diameter of the pipe 42 is reduced compared to a diameter of the pipe 42 due to the deposit formation. It is also thinkable that the device for detection deposit formation 8 comprise a further detection mean that may identify the deposit. Such a further detection means may identify scale, fouling and/or corrosion. In particular it is provided that the device for detecting deposit formation 8, in particular scaling, detects an increase in scaling or a growth of scaling and subsequently the concentration of the antiscaling product inside the liquid bearing system 100 is increased immediately after the time interval.

REFERENCE SIGNS 1 main system
2 subsystem/bypass
3 pipe of the main system
3' pipe of the subsystem
4 pumping device
5 liquid
7 transport direction in main system
7' transport direction in subsystem
8 detection device
10 reflection area
20 emitted ultrasonic signal
21 reflected ultrasonic signal
51 center line
41 diameter of pipe
42 effective diameter of the pipe
60 deposit
69 first distance
70 temperature
71 third distance
72 second distance
73 distance
74 second temperature
75 first temperature
76 temperature at the wall of the pipe
77 temperature of the liquid
78 temperature at the heater
80 heater
81 first means for measuring the first temperature
82 second means for measuring the first temperature
83 isolation
100 liquid bearing system

We claim:

1. A method for controlling deposit (60) formation in a liquid (5) bearing system (100) comprising a main system (1) and a subsystem (2), wherein the liquid (5) is transported inside the main system (1) and a subsystem (2), wherein the subsystem (2) is designed as a bypass, the method comprising the step of altering a property of the liquid (5) inside the subsystem (2) such that it differs from the property of the liquid (5) inside the main system (1) in a manner that deposit (60) formation inside the subsystem (2) is more promoted than inside the main system (1), wherein a first flow velocity of the water (5) inside the subsystem (2) is configured such that the first flow velocity inside the subsystem (2) is greater than a second flow velocity inside the main system (1), wherein the first flow velocity inside the subsystem is realized by a pumping device, and wherein the deposit (60) formation is detected by a detection device (8) inside the subsystem (2) and treating the water bearing system (100) once a deposit (60) inside the subsystem (2) is detected.

2. The method according to claim 1, wherein at least one property of the liquid (5) inside the subsystem (2) is manipulated by a manipulation device.

3. The method according to claim 1, wherein liquid (5) inside the subsystem (2) is configured such that a Reynolds number of the liquid (5) inside the subsystem (2) is greater than 8,000 and preferably between 10,000 and 20,000.

4. The method according to claim 1, wherein a first flow velocity of the liquid (5) inside the subsystem (2) is configured such that the first flow velocity inside the subsystem (2) is greater than a second flow velocity inside in the main system (1).

5. The method according to claim 4, wherein the first flow velocity inside the subsystem (2) is mainly realized by a pumping device (4).

6. The method according to claim 1, wherein the deposit (60) formation is detected by means of ultrasound, wherein an ultrasonic signal is emitted and a reflected ultrasonic signal is detected.

7. The method according to claim 1, wherein the temperature inside the subsystem (2) is monitored.

8. The method according to claim 1, wherein the subsystem (2) comprises a heater (80).

9. The method according to claim 1, wherein the liquid bearing system (100) comprises a device for monitoring the temperature, wherein the device is arranged at a wall of a pipe (3,3'), that guides the liquid (5), wherein the device for monitoring the temperature at the wall of the pipe (3,3') comprises a first means (81) for measuring a first temperature (75) at a first spot and a second means (82) for measuring a second temperature (74) at a second spot, wherein the first spot is spaced from the wall of the pipe by a first distance (69) and the second spot is spaced from the wall of the pipe by a second distance (72), wherein the second distance is greater than the first distance and wherein the temperature inside the pipe (3,3') is approximated based on the first temperature (75) and the second temperature (74).

10. The method according to claim 1, wherein a treatment chemical is fed to the liquid bearing system (100) as soon as a deposit (60) inside the subsystem (2) is detected.

11. The method according to claim 1, wherein the liquid bearing system (100) is a cooling water system having an outflow and an inflow, wherein water is transported inside the main system (1) and a subsystem (2), wherein the subsystem is designed as a bypass, the method comprising the step of altering a property of the water (5) inside the bypass (2) such that it differs from the property of the water (5) inside the main system (1) in a manner that scaling (60) formation inside the subsystem (2) is more promoted than inside the main system (1), wherein a first flow velocity of the liquid (5) inside the subsystem (2) is greater than a second flow velocity inside the main system (1), wherein the Reynolds number of the water inside the subsystem (2) is between 10,000 and 20,000, wherein the scaling formation inside the subsystem (2) is detected by means of ultrasound, wherein an ultrasonic signal is emitted and a reflected ultrasonic signal is detected.

12. A device for controlling deposit (60) formation in a liquid (5) bearing system (100) comprising a main system (1) and a subsystem (2), wherein a liquid (5) is transportable inside the main system (1) and subsystem (2), wherein the device is configured for altering a property of the liquid (5) such that it differs from the property of the liquid (5) inside the main system (1) in a manner that deposit (60) formation inside the subsystem (2) is more promoted than inside the main system (1); and wherein mounted inside the subsystem (2) is a device configured to detect the formation of a deposit in the subsystem; and wherein treatment chemicals are fed to the water bearing system (100) once a deposit (60) inside the subsystem (2) is detected.

13. An upgrade kit for a liquid (5) bearing system (100) comprising a main system (1) and a subsystem (2), wherein the subsystem (2) has access to the liquid (5) of the main system (1); and wherein the subsystem (2) comprises a device is configured to detect the formation of a deposit and altering a property of the liquid (5) inside the subsystem (2) such that it differs from the property of the liquid (5) inside the main system (1) in a manner that deposit (60) formation inside the subsystem (2) is more promoted than inside the main system (1).

* * * * *